United States Patent [19]

Pinson

[11] 4,246,661
[45] Jan. 27, 1981

[54] DIGITALLY-CONTROLLED ARTIFICIAL HAND

[75] Inventor: George T. Pinson, Huntsville, Ala.

[73] Assignee: The Boeing Company, Seattle, Wash.

[21] Appl. No.: 20,575

[22] Filed: Mar. 15, 1979

[51] Int. Cl.³ .............................. A61F 1/00; A61F 1/06
[52] U.S. Cl. ............................................ 3/1.1; 3/12.5; 3/12.7
[58] Field of Search ............................ 3/1.1, 12–12.8

[56] References Cited

U.S. PATENT DOCUMENTS

| | | | |
|---|---|---|---|
| 809,797 | 1/1906 | Grogan | 3/12.6 |
| 1,499,052 | 6/1924 | Carson | 3/12 UX |
| 2,422,302 | 6/1947 | Horn | 3/12.4 |
| 2,580,987 | 1/1952 | Alderson | 3/1.1 |
| 3,466,937 | 9/1969 | Motis | 3/12.5 X |
| 3,694,021 | 9/1972 | Mullen | 3/12.7 X |

Primary Examiner—Ronald L. Frinks
Attorney, Agent, or Firm—Thomas H. Murray

[57] ABSTRACT

An artificial forearm and hand having a fully-articulated wrist motion. The invention provides an integrated digitally-controlled remote manipulator device capable of reproducing all of the major motions of the human forearm, wrist and hand in a cmpact in-line package. This motion is accomplished without the requirement for feedback thereby making the invention ideally suited to digital computer control. The packaging of the device permits it to be sealed, meaning that it can be used as a remote manipulator that can reproduce human arm and hand motions. The packaging also produces a lightweight, cosmetically pleasing prosthetic device for use by humans.

12 Claims, 11 Drawing Figures

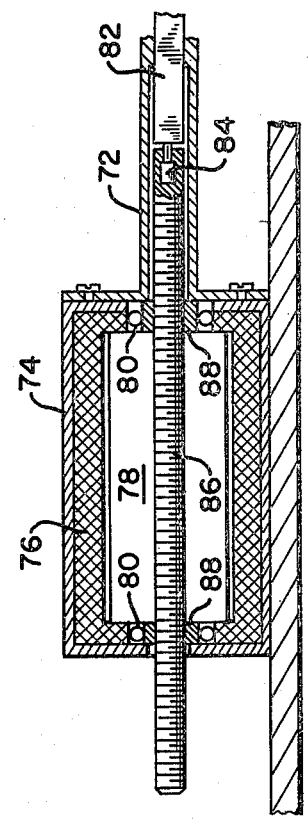
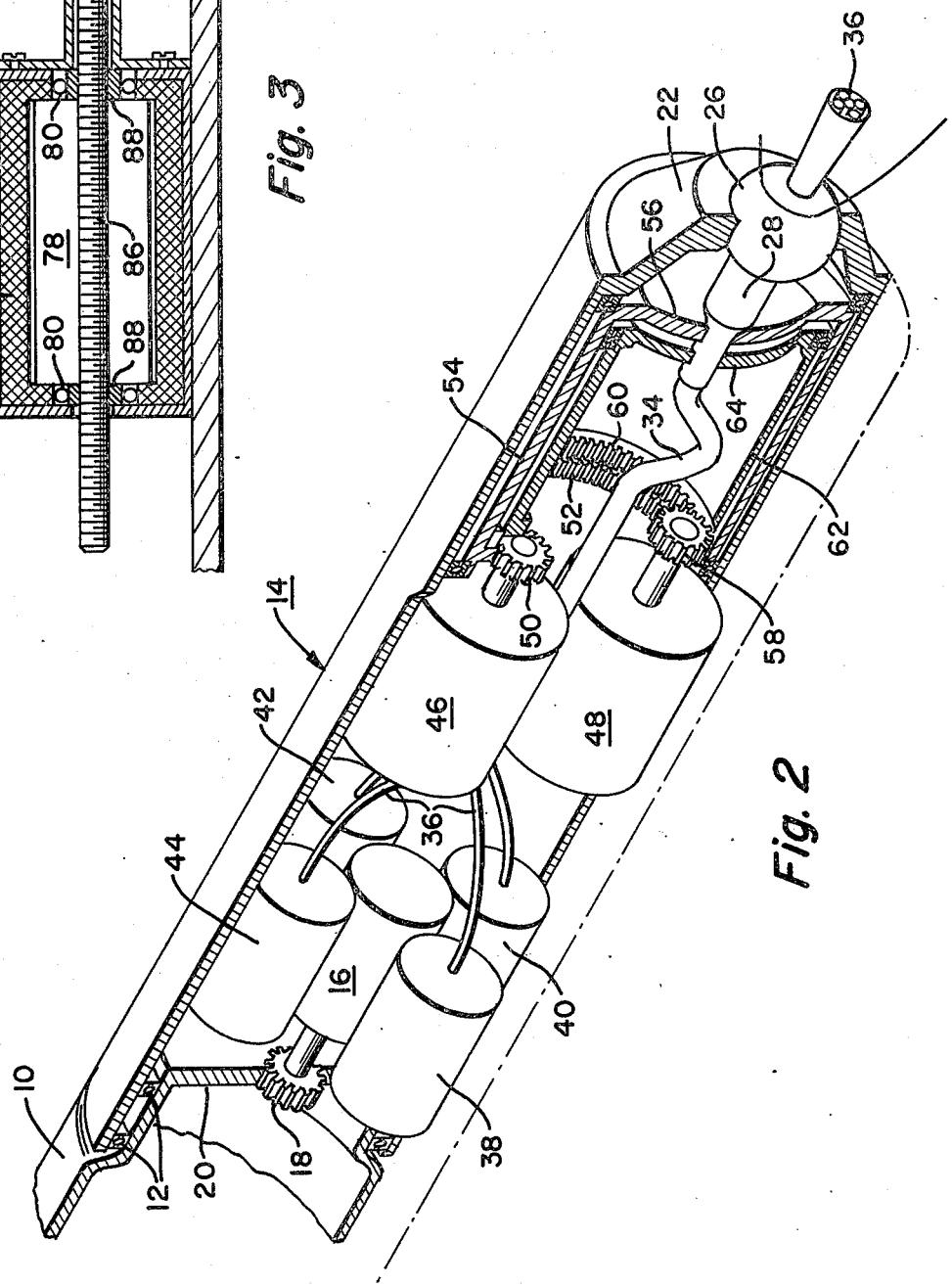
Fig. 3
Fig. 2

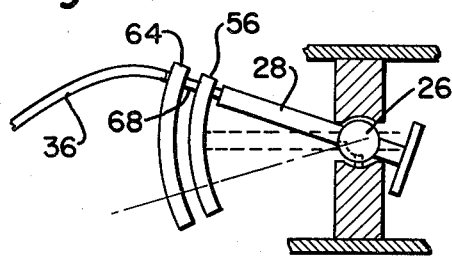
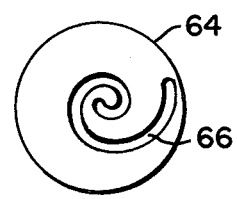
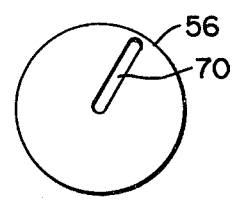
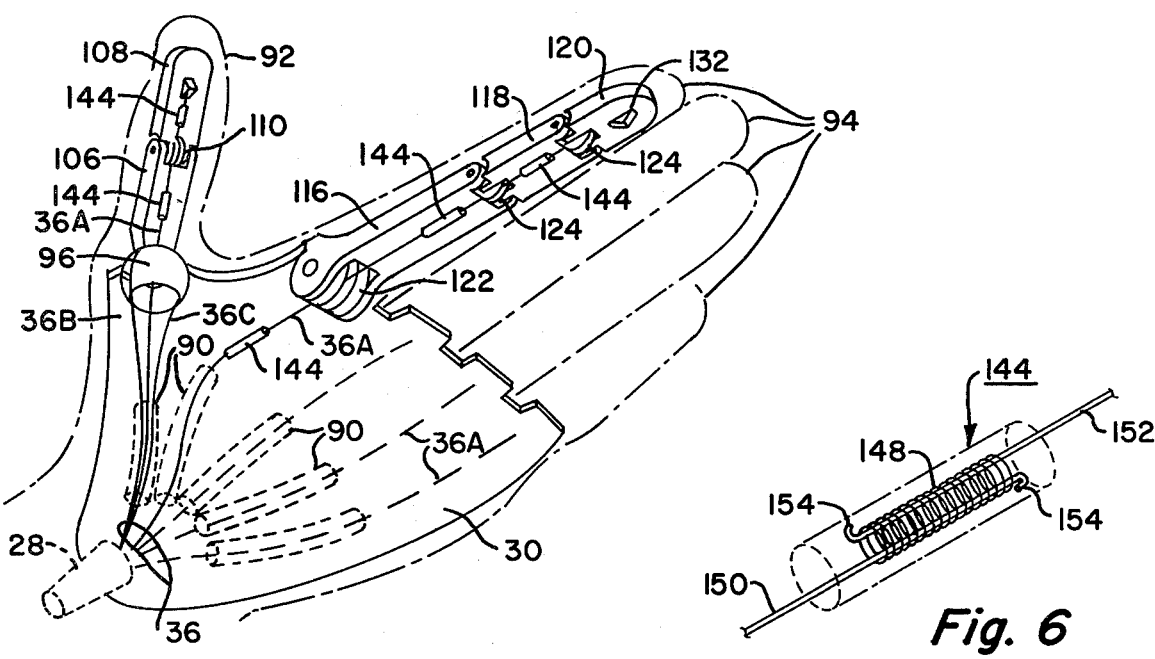
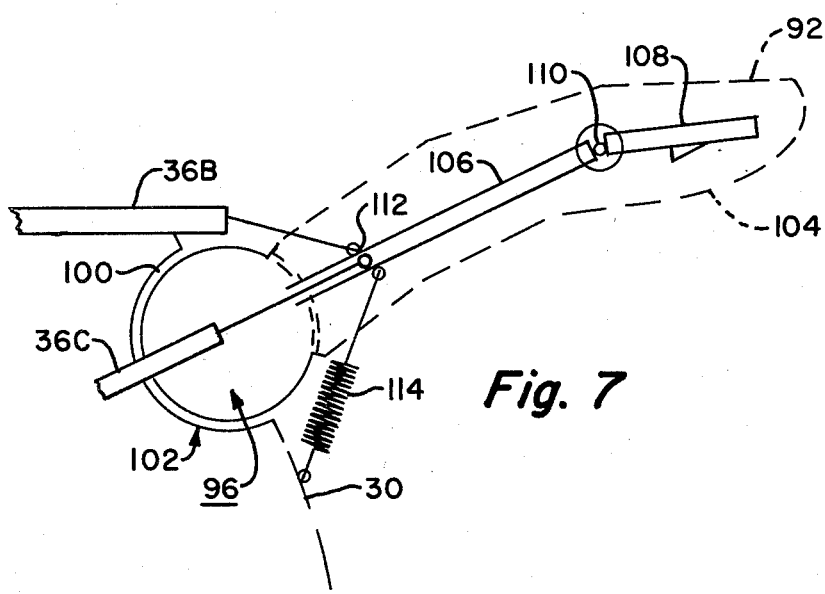

DIGITALLY-CONTROLLED ARTIFICIAL HAND

BACKGROUND OF THE INVENTION

As is known, most artificial or prosthetic arm and hand devices are clumsy, have severe motion limitations, and are unnatural in appearance. While remote manipulators similar to the forearm and hand have been used in space, planetary exploration, deep-sea work and in nuclear research, these suffer primarily from cost, controllability and an inability to reproduce human arm and hand motions. In this respect, most remote manipulators of the foregoing types, including the prosthetic devices, are unable to perform wrist motion in a compact mechanism. Designers have approached the problem along two separate lines. The first, and most common approach, is not to use wrist motion at all. This is most easily visualized by the "claw" or "hook" type of prosthetic. In the absence of wrist motion, the claw must be rotated about the axis of the arm to align the claw with the object to be grasped. This motion must be followed by orienting the arm such that the object picked up can be held at an acceptable angle relative to vertical.

Where size, weight and cost are not constraints and the degree of freedom provided by wrist motion is necessary, a gimbaled, azimuth/elevation type of wrist joint is used. However, only a two degree of freedom gimbaled wrist manipulator can duplicate the total wrist motion. Even if a two degree of freedom gimbaled arrangement is utilized, the required placement of the drive motors for the manipulator results in a rather large and bulky package.

SUMMARY OF THE INVENTION

In accordance with the present invention, a prosthetic forearm and hand device is provided comprising a forearm portion adapted for connection to the remainder of a severed arm, and a palm portion connected to the lower end of the forearm portion through a ball and socket connection. Means are provided for manipulating the hand portion about the center of the ball and socket connection and achieve simultaneous universal movement along two vectors at right angles to each other. A thumb is connected to the palm portion through a ball and socket connection, the thumb having a pivoted joint between the ball and socket connection and its extremity. Fingers are connected to the palm portion with each finger having two pivoted joints therein. Spring devices normally hold the thumb and fingers in extended positions; while motor means in the forearm are provided for manipulating the thumb and fingers about their pivoted joints. Cable devices are provided for connecting the extremity of the thumb and each of the fingers to an associated one of the motor devices.

In the preferred embodiment of the invention, the thumb and the fingers are held in their extended positions about pivoted joints by the aforesaid spring devices; while the motor means for the thumb and fingers in the forearm preferably comprises digital stepping motors, the arrangement being such that upon movement of the stepping motors in one direction, the thumb and/or fingers will be curved inwardly against the force of the springs. However, upon movement of the stepping motors in the opposite direction, the springs will automatically extend the thumb and/or fingers without the need for an electrical servo feedback loop.

The above and other objects and features of the invention will become apparent from the following detailed description taken in connection with the accompanying drawings which form a part of this specification, and in which:

FIG. 2 is an enlarged broken-away perspective view of the forearm portion of the prosthetic device of FIG. 1;

FIG. 3 is a cross-sectional view illustrating one type of stepping motor that can be used in the prosthetic device of the invention;

FIG. 4A illustrates the wrist motion mechanism of the prosthetic device of FIG. 1;

FIG. 4B is an illustration of the spiral drive utilized in the mechanism of FIG. 4A;

FIG. 4C is an illustration of the slotted rotary drive used in the mechanism of FIG. 4A;

FIG. 5 is an enlarged perspective view of the hand portion of the prosthetic device of FIG. 1;

FIG. 6 is an enlarged illustration of the spring devices utilized in controlling the thumb and fingers shown in FIG. 5;

FIG. 7 is an illustration of the manner in which the thumb is connected to a palm portion by a ball and socket connection;

Figure 1:
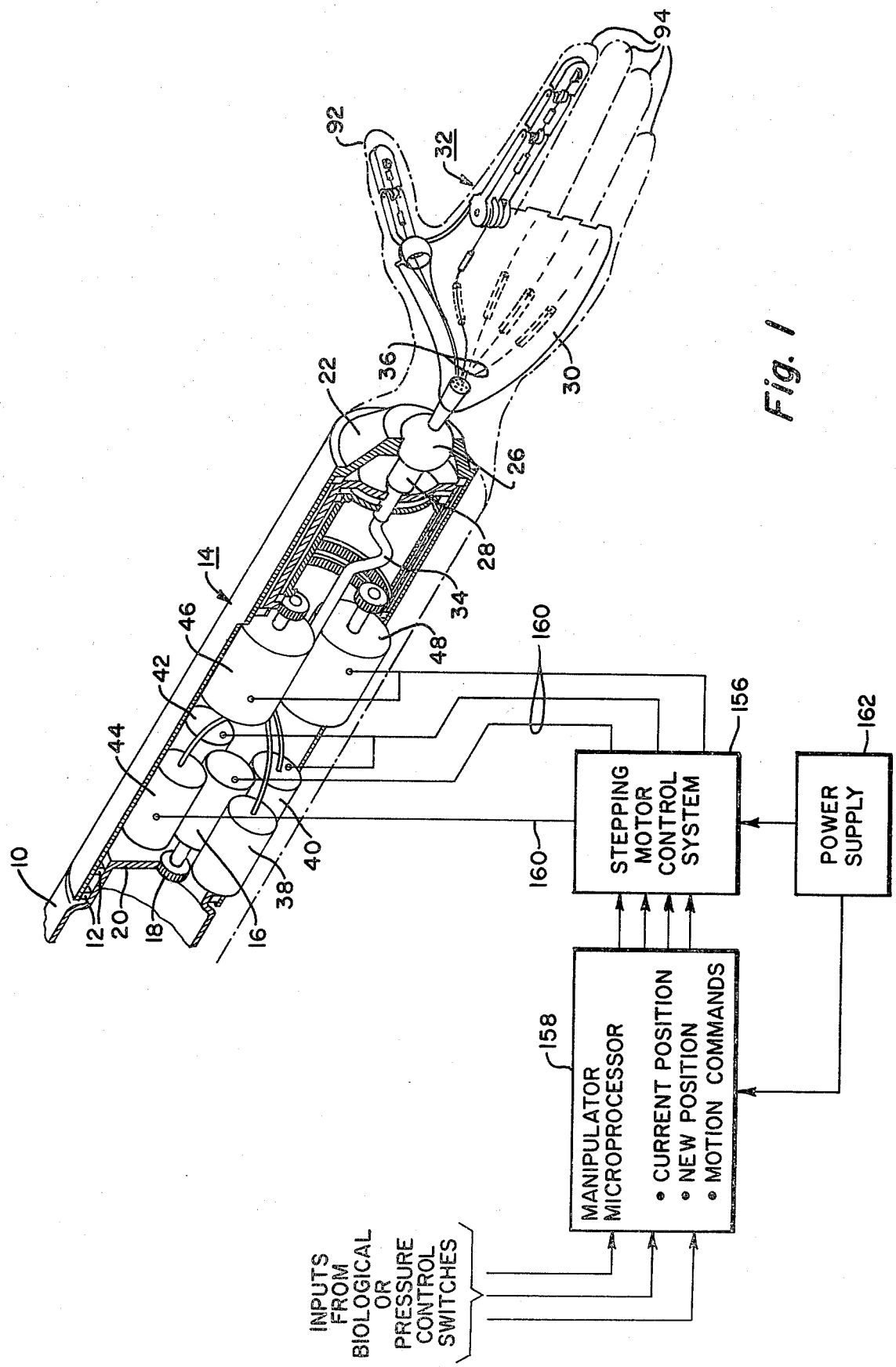
FIG. 1 is a partially broken-away perspective view of the prosthetic device of the invention.

With reference now to the drawings, and particularly to FIG. 1, there is provided a support member 10 adapted for connection to the end of a severed limb, for example, or to whatever structural point is required to meet the particular application needs. The support member 10 is provided with a reduced diameter portion which supports ball bearings 12. The bearings 12, in turn, carry a cylindrical forearm portion 14 such that the forearm may be rotated about the center line of the bearings 12 relative to the support member 10. Carried within the hollow forearm 14 is a forearm stepping motor 16 connected to a forearm drive gear 18 (FIG. 2) secured to a circular plate 20 which forms part of the support member 10, the arrangement being such that as the armature of the stepping motor 16 rotates, and assuming that the support member 10 is stationary, the entire cylindrical forearm portion 14 will be caused to rotate about the axis of the stepping motor 16. Actually, the gear 18 can be replaced by a rigid connection between the drive shaft of stepping motor 16 and the plate 20.

Carried at the forward end of the hollow forearm portion 14 is a spider 22 which supports a ball and socket joint 26. The ball of the joint 26, in turn, has a hollow shaft 28 extending therethrough and this shaft supports the palm portion 30 of a hand assembly 32, hereinafter described in detail. Extending through the hollow shaft 28 and a flexible joint 34 within the hollow forearm portion 14 are control cables 36. As will hereinafter be described in greater detail, respective ones of the cables 36 are connected to an associated one of four stepping motors 38, 40, 42 and 44. Motor 38 is a thumb stepping motor; motors 40 and 42 are thumb/finger flexure control stepping motors; and motor 44 is a thumb rotation control stepping motor. Also contained within the hollow forearm 14, as perhaps best shown in FIG. 2, are two wrist drive stepping motors 46 and 48.

As best shown in FIG. 2, the stepping motor 46 is provided with an output pinion gear 50 which meshes with an internal ring gear 52 carried at one end of an outer, rotatable cylindrical member 54 which carries at its opposite end a slotted disc 56. In a similar manner, the stepping motor 48 is provided with an output drive pinion gear 58 which meshes with an internal ring gear 60 carried at one end of an internal, rotatable cylindrical member 62. The end of member 62 opposite the ring gear 60 carries a disc or plate 64 having a spiral groove formed therein.

The details of the plates 56 and 64 and the ball and socket joint 26 are shown schematically in FIGS. 4A-4C. First, with reference to FIG. 4B, the plate 64 has a spiral slot 66 therein through which shank portion 68 of the hollow shaft 28 carried by ball and socket joint 26 extends. Plate 56 is shown in FIG. 4C and has a radially-extending slot 70 formed therein. The shank portion 68 of the hollow shaft 28 also extends through the slot 70. It will be appreciated that with plate 64 stationary while plate 56 rotates, and assuming that the reduced diameter portion 68 is in the spiral slot 66 other than at its center, a spiral motion will be effected to the end of the shaft 28. In like manner, if plate 56 is held stationary while plate 64 rotates, linear movement of the shaft 28 along the direction of slot 70 will result. Furthermore, by appropriate simultaneous rotation of the two plates 56 and 64, the end of shaft 28 opposite the plates 56 and 64 can be moved to any point in a plane extending perpendicular to the axis of the forearm 14.

With reference, again, to FIG. 1, it will be noted that the palm plate 30 is connected to the end of shaft 28 opposite the plates 56 and 64. Consequently, the palm and the entire hand 32 mat be moved to any angular position and location with respect to the axis of the forearm 14 by appropriate rotation of the two plates 56 and 64 by the stepping motors 46 and 48.

The thumb/finger stepping motors 38-44 differ from a conventional stepping motor as shown in FIG. 3. The cable housings 72 for each of the cables 36 are connected to the case 74 of the motor which is provided with field windings 76 and an armature 78 rotatable in bearings 80. The inner cable 82, at a point removed from the case 74 is square in cross section and is connected through a rotary joint 84 to a threaded member 86 which passes through threaded worm gear followers 88 at opposite ends of the armature 78. The armature, it will be noted, is hollow such that the threaded portion 86 may pass therethrough. With this arrangement, and as the armature 78 rotates, rotation of the worm gear followers 88 will cause the threaded member 86, as well as the cable 82, to move to the right or left depending upon the direction of rotation of the armature 78. Assuming that the armature 78 moves in steps, so also will the cable 82 move to the right or left in steps. As a result, armature motion will either pull or push the cable 82, thereby varying the position of the fingers or thumb of the hand 32 (FIG. 1) in a manner hereinafter described.

Another view of the hand 32 is shown in FIG. 5. The control cables 36 emerging from the hollow shaft 28 are routed through cable guides 90 mounted on the palm plate 30 which, in turn, is carried on the end of the hollow shaft 28 passing through the ball and socket joint 26 as described above. There are five cables 36A connected to the extremities of the thumb 92 and each of the four fingers 94. For simplicity, the details of the thumb 92 and only the index finger 94 are shown in FIG. 5. The cables 36A, in turn, are actuated by the thumb/finger flexure control stepping motors 40 and 42. The thumb stepping motors 38 and 44 are connected to cables 36B and 36C which operate a ball thumb joint 96. The details of the joint 96 are shown in FIG. 7. The ball 100 of joint 96 is carried within a spherical receptacle 102 formed in the palm plate 30.

The thumb 92 comprises an outer, surrounding material 104 of plastic or the like which simulates the appearance of skin. Contained within the cover 104 is a first linkage 106 securely fastened to the ball 100 and an outer linkage 108 hinged to the linkage 106 at 110. The details of hinge 110 will hereinafter as described in detail. The two cables 36B and 36C are secured to the linkage 106 at attachment point 112 to give the necessary amount of leverage to move the linkage 106 and, hence, the thumb 92 in two directions at right angles to each other. A return spring 114 is connected between attachment point 112 and the palm plate 30 to act against the force exerted by the pull of cable 36B. A similar spring device, not shown, is connected between the attachment point 112 and the palm plate 30 to counteract the pulling force exerted by cable 36C from one of the two stepping motors 38 or 44. It will be appreciated, therefore, that whenever the tension is relaxed on the cable 36B or 36C, the springs 114 will automatically retract the thumb 92 into a position where it is folded against the palm of the hand. When tension is again exerted by the cables 36B and 36C, however, the thumb will then move in the ball joint 96 to a position dictated by the number of steps executed by the respective stepping motors 38 and 44.

Figure 8:
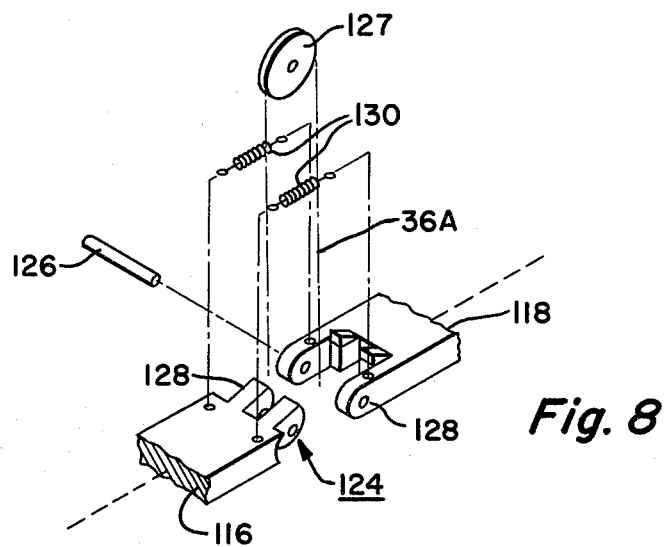
FIG. 8 is an exploded view of the hinged joint used in the fingers of the hand portion shown in FIG. 5.

As shown in FIG. 5, each of the fingers 94 has an outer prosthetic covering, resembling skin, which contains three linkages 116, 118 and 120. Linkage 116 is connected to the palm plate 30 through a knuckle joint 122 while the other end of linkage 116 is connected to linkage 118, and linkage 118 is connected to linkage 120 through finger joints 124. Thumb joint 110 is the same as joints 124. The details of each of the finger joints 124 are shown in FIG. 8. A hinge pin 126 passes through a pulley 127 and holes provided in cooperating lugs 128. A cable 36A, which passes beneath the linkages 116 and 118 passes upwardly and over the pulley 127 and thence under the next successive linkage. Return springs 130 are connected between the ends of the respective linkages 116 and 118, for example, for normally maintaining the linkages 116-118 and, hence, the entire finger 94 is an extended position. When, however, tension is exerted by a cable 36A connected to the forward linkage 120 at cable attachment point 132 (FIG. 5), the linkages 116-120 will begin to fold upon themselves.

Figure 9:
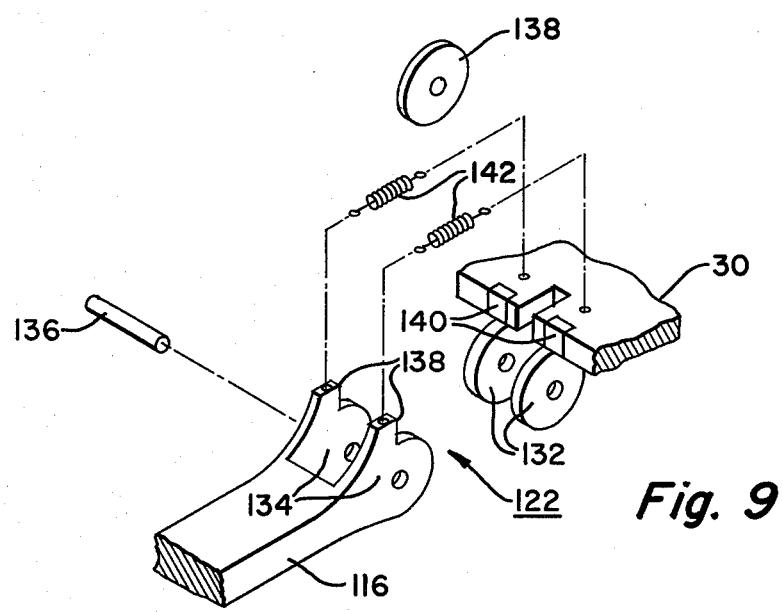
FIG. 9 is an exploded view of the hinged joint forming the knuckle connection to the finger of FIG. 5.

The details of the knuckle joint 122 are shown in FIG. 9. The palm plate 30 is provided with downwardly-projecting lugs 132 which mate with lugs 134 on the linkage 116. A hinge pin 136 spins through holes in the lugs 132 and 134 as well as a pulley 138, positioned between the lugs. The lugs 134 are provided with projections 138 adapted to engage pressure pads 140 fitted into slots in the palm plate 30. As in the knuckle joint shown in FIG. 8, return springs 142 extend between the linkage 116 and the palm plate 30 to hold the linkage 116 is extended position.

Spaced along each of the cables 36A are spring assemblies 144, the details of which are shown in FIG. 6. Each spring assembly 144 comprises a coil spring 148 through which the ends of cable sections 150 and 152 extend. The ends of the cable sections 150 and 152 are hooked as at 154 and engage the opposite ends of the coil spring 148, the arrangement being such that upon separating movement of the two cable sections 150 and 152, the spring 148 will compress.

In operation, as the control cable 36A is shortened by one of the stepping motors 40 or 42, the fingers 94 or thumb 92 will begin to bend inwardly about the joints 122, 124, for example. As each finger 94 contacts the surface of an object to be grasped, the coil springs 148 and spring assemblies 144 will begin to compress; however other fingers and/or the thumb continue to curve inwardly. As they, in turn, contact the surface, their spring assemblies 144 begin to compress until the springs are completely compressed. The lengths of the springs 148 are selected to permit the thumb 92 and all fingers to touch and grasp an object. The force applied is a function of the motor power and the amount of force required is determined by the input motion commands.

Reverting again to FIG. 1, each of the stepping motors 38-48 is connected to a stepping motor control system 156 connected to a microprocessor 158 which actuates the stepping motors to achieve any selected geometrical configuration of the wrist and hand in response to the input motion commands on leads 160. The input motion commands may be supplied by any well known conventional means such as pressure switches attached to the portion of the arm which has not been amputated and actuable by flexure of selected muscles. A power supply 162 supplies power to each of the circuits 156 and 158.

Although the invention has been shown in connection with a certain specific embodiment, it will be readily apparent to those skilled in the art that various changes in form and arrangement of parts may be made to suit requirements without departing from the spirit and scope of the invention.

I claim as my invention:

1. A prosthetic forearm and hand device comprising a forearm portion adapted for connection to the remainder of a severed arm, a palm portion connected to the lower end of said forearm portion through a ball and socket connection, means for manipulating said hand portion about the center of said ball and socket connection to achieve simultaneous movement along two vectors at right angles to each other, a thumb connected to said palm portion through a ball and socket connection, said thumb having a pivoted joint therein, fingers pivotally connected to said palm portion, each finger having two pivoted joints therein, spring devices normally holding said thumb and fingers in extended positions, motor devices in said forearm for manipulating said thumb and fingers about their pivoted joints, and cable means connecting the extremity of said thumb and each of said fingers to an associated one of said motor devices.

2. The device of claim 1 wherein said motor devices each comprises a stepping motor.

3. The device of claim 1 wherein said spring devices span said pivoted joints and are connected at their opposite ends to links forming part of a finger or thumb.

4. The device of claim 1 including expansion spring devices included in each of said cable means.

5. The device of claim 1 wherein the pivoted finger joints each includes a pulley over which said cable means passes.

6. The device of claim 1 wherein said motor means includes two stepping motors for rotating said thumb in its ball and socket connection to said palm plate and at least one stepping motor for pulling said cable means to curve said fingers inwardly toward the palm portion against the force of said spring devices.

7. In a prosthetic device capable of reproducing motions of a human body member, the combination comprising a hollow prosthetic forearm, a prosthetic attachment to said forearm to which the reproduced motion is imparted, a shaft with said attachment secured to one end of said shaft, ball and socket joint means mounting said shaft to said forearm intermediate the ends of said shaft for pivoting said prosthetic attachment about an end of said forearm, means adapted to move the end of said shaft opposite said prosthetic attachment and within the interior of said forearm, and means to control said means of motion responsive to the prosthesis wearer.

8. The device of claim 7 wherein said control means is responsive to muscular activity of the prosthesis wearer.

9. The apparatus of claim 8 wherein said control means includes biomechanical microswitches responding to muscle activity of the prosthesis wearer.

10. The device of claim 7 wherein said prosthetic device is a substitute for a portion of the human arm, said prosthetic attachment is a substitute for the human hand, and said device reproduces the motion of the human wrist.

11. The device of claim 7 wherein said means adapted to move the end of said shaft opposite said prosthetic attachment within the interior of said forearm includes means to independently impart motion along a linear arc about said shaft mounting means to said prosthetic attachment and a rotating motion about the central axis of said forearm to said prosthetic attachment.

12. The device of claim 7 wherein said means adapted to move the end of said shaft opposite said attachment includes a rotatable member mounted for rotation about the central axis of said forearm and having a face formed with a generally spiral groove which receives the end of said shaft opposite said prosthetic attachment, a member mounted for rotation about the central axis of said forearm between said spirally-grooved member and said shaft mounting means with a slot formed in said member extending radially outwardly from the central axis of said forearm and through which the shaft extends, and separate means for independently rotating said spirally-grooved and slotted members.

* * * * *